US007065219B1

(12) United States Patent
Abe et al.

(10) Patent No.: US 7,065,219 B1
(45) Date of Patent: Jun. 20, 2006

(54) ACOUSTIC APPARATUS AND HEADPHONE

(75) Inventors: Kensaku Abe, Tokyo (JP); Kazuhisa Kito, Tokyo (JP); Hirofumi Nishimoto, Tokyo (JP); Keiko Yabuki, Tokyo (JP)

(73) Assignee: Sony Corporation (JP)

( * ) Notice: Subject to any disclaimer, the term of this patent is extended or adjusted under 35 U.S.C. 154(b) by 0 days.

(21) Appl. No.: 09/529,269

(22) PCT Filed: Aug. 12, 1999

(86) PCT No.: PCT/JP99/04377

§ 371 (c)(1),
(2), (4) Date: Oct. 10, 2000

(87) PCT Pub. No.: WO00/10362

PCT Pub. Date: Feb. 24, 2000

(30) Foreign Application Priority Data

Aug. 13, 1998 (JP) ............................... P10-228759

(51) Int. Cl.
*H04R 1/10* (2006.01)
(52) U.S. Cl. .......................................... 381/74; 381/26
(58) Field of Classification Search .................. 381/74, 381/72, 71.1, 71.6, 71.8, 71.7, 26, 309
See application file for complete search history.

(56) References Cited

U.S. PATENT DOCUMENTS 4,088,849 A * 5/1978 Usami et al. ............... 379/430
4,819,270 A * 4/1989 Lombardo ................... 381/26
4,928,311 A * 5/1990 Trompler ..................... 381/72
5,182,774 A * 1/1993 Bourk .......................... 381/71
5,251,263 A * 10/1993 Andrea et al. ............... 381/71
5,341,254 A * 8/1994 Ueno ........................... 360/62
5,815,582 A * 9/1998 Claybaugh et al. ........ 381/71.6
5,937,070 A * 8/1999 Todter et al. .............. 381/71.6
5,987,147 A * 11/1999 Nishimoto ................... 381/375

FOREIGN PATENT DOCUMENTS

| EP | 0282017 | * | 9/1888 |
| JP | 62-013199 | * | 1/1987 |
| JP | 05-333872 | * | 12/1993 |
| JP | 5-333873 | * | 12/1993 |

* cited by examiner

Primary Examiner—Vivian Chin
Assistant Examiner—Lun-See Lao
(74) Attorney, Agent, or Firm—Lerner, David, Littenberg, Krumholz & Mentlik, LLP

(57) ABSTRACT

A headphone section 10 having microphone elements 14L, 14R for detecting a sound around the user and signal acoustic transducing elements 15L, 15R which function as a sound source for canceling the sound around the user housed in the headphone boxes 13L, 13R and a control circuit section 20 that includes a noise canceling headphone together with the headphone section 10 are separately configured. The control circuit section 20 is adjusted in such a manner that variation can be reduced and predetermined frequency characteristics and gain characteristics are achieved at a predetermined frequency. To the headphone section 10, gain adjusting sections 16L, 16R are equipped.

10 Claims, 7 Drawing Sheets

ACOUSTIC APPARATUS AND HEADPHONE

TECHNICAL FIELD

The present invention relates to a headphone and acoustic apparatus which reduce noise from the surroundings and make it easier to listen to, for example, music.

BACKGROUND ART

There is known a so-called noise canceling headphone which can reduce noise of the surroundings by collecting noise around the user by a microphone with a headphone incorporated into a housing, analyzing the noise, and outputting a negative phase sound from the signal-audio converter element (hereinafter called the "driver unit") of the headphone.

In this case, as for the noise canceling system, two types are available: a feed-forward system and feedback system. FIG. 9 shows a configuration of the noise canceling headphone of the feed-forward system, while FIG. 10 shows a configuration of the noise canceling headphone of the feedback system.

In the feed-forward system of FIG. 9, the microphone element is arranged at such a location that a noise around the microphone element is collected but a sound released from the driver unit 2 is not collected. The electric signal from the microphone element 1 corresponding to the surrounding noise collected is supplied to the equalizer circuit 3.

This equalizer circuit 3 has a phase and amplitude characteristic, that is, a frequency characteristic, optimally designed in order to obtain an audio signal for canceling the surrounding noise inputted. An output signal of the equalizer circuit 3 is supplied to an AMP 5 via an adder circuit 4.

This AMP 5 is optimally designed so that the gain of the audio signal for canceling the sounding noise becomes optimal. The audio signal for canceling the surrounding noise from the AMP 5 is supplied to the driver unit 2. That is, the driver unit 2 functions as a sound source for canceling the surrounding noise of the user.

As described above, the sound of a phase negative to that of the surrounding noise is emitted in the vicinity of user's ears and is acoustically synthesized with the surrounding noise. As a result, the surrounding noise is canceled and the sound with reduced surrounding noise is listened to by the user.

In the case such as this, from an audio signal input terminal 6, music signals, etc. are supplied, added at the adder circuit 4, and supplied to the driver unit 2 via the AMP 5, and music is played back. At this time, the user can comfortably enjoy high-quality music without excessively turning up the volume even if the surrounding noise is large, because it is canceled and reduced as described above.

Next, in the feedback system of FIG. 10, the microphone element 1 collects the synthesized sound between the surrounding noise and the sound emitted from the driver unit 2 near the user's ears. The the frequency characteristics (phase and amplitude characteristics) of the equalizer circuit 3 are optimally designed in such a way that the synthesized sound collected by the microphone element 1 becomes below a predetermined level. The gain of AMP 5 is also designed to achieve optimum canceling effects on the surrounding sound.

In the feedback system, as shown in FIG. 10, the adder circuit 4 is mounted on the input side of the equalizer circuit 3. And the music signal, etc. is supplied from the audio signal input terminal 6, added at the adder circuit 4, and supplied to the driver unit 2 via the equalizer circuit 3 and the AMP 5, and the music is played back. In this event, the user can comfortably enjoy the high-quality music without excessively turning up the volume because the surrounding noise is canceled as described above even if it is noisy.

Because the noise canceling headphone has the above-mentioned advantages, it is utilized for listening to the music in the aircraft with engine noises reduced.

However, a conventional noise canceling headphone has a component element for noise canceling, which is structured to be integral with a headphone section in such a way that it is practically inseparable from the headphone section. The reason for the integral structure is that the noise canceling headphone creates the negative phase component of the noise signal over a broad band exceeding 1 decade and cancels the noise from the viewpoint of the operating principle, but because of large variations of audio characteristics as well as for absorbing the variations of individual noise canceling component elements, all the elements are integrated into one and comprehensively adjusted and corrected to maximize the canceling effects.

However, this kind of integral structure has following problems:

1) Even when part of the component elements, such as ear pads that come in contact with the human body, must be replaced for hygienic reasons, the whole must be replaced;
2) When part of the component elements is replaced, the whole must be adjusted again; and
3) Whether the whole or part is replaced, the maintenance expenses generated in the case become great.

It is an object of the present invention to provide an acoustic apparatus that can clear away the problems as mentioned above.

DISCLOSURE OF THE INVENTION

In order to solve the above-mentioned problems, an acoustic apparatus according to the present invention is characterized by comprising; a headphone section to be mounted on a user head, which has the microphone element for detecting sound around the user and a signal acoustic transducing element with a function as a sound source for canceling the sound around the user housed in a headphone box, and is equipped with a first output terminal for outputting the audio signal collected by the microphone element and a first input terminal for inputting the audio signal supplied to the signal acoustic transducing element, and a control circuit section independent from the headphone section, equipped with the second input terminal connected to the first output terminal and the second output terminal connected to the first input terminal, and intended to control at least the frequency characteristics and the gain characteristics of the audio signal from the microphone element of the headphone section inputted through the second input terminal, to generate a signal that can serve as a sound source for canceling the surrounding sound, and to supply the signal to the signal acoustic transducing element of the headphone section through the second output terminal.

Because the headphone section and the control circuit section for generating the signal for canceling the surrounding sound are formed independently, even when part of component elements is replaced, the whole does not need to be replaced. In addition, even if part of the headphone section or control circuit section is replaced, adjustment is required only of the headphone section or control section to which the said partial replacement is carried out, and the adjustment operation becomes easy and the maintenance expenses can be reduced.

The noise canceling headphone and the acoustic apparatus according to the present invention are characterized in that an adjusting section is provided for adjusting the volume to be canceled of the surrounding sound in the headphone box.

Even when the headphone section and the control circuit section are composed separately, by providing an adjusting section at the headphone section suitable adjustment can be achieved as a noise canceling headphone apparatus.

In addition, the noise canceling headphone and the acoustic apparatus according to the present invention are characterized by frequency characteristics and gain characteristics of the control circuit section being adjusted to predetermined levels at a predetermined frequency within a range of 50 Hz to 1.5 kHz.

Because adjustments are made in the way that the control circuit section itself is nearly free from any variations, even if the two sections are separate, they can be configured to exhibit the predetermined noise canceling effects particularly by combinations.

BEST MODE FOR CARRYING OUT THE INVENTION

Hereinafter, embodiments of the acoustic apparatus according to the present invention will be described in detail by referring now to accompanying drawings.

Figure 1:
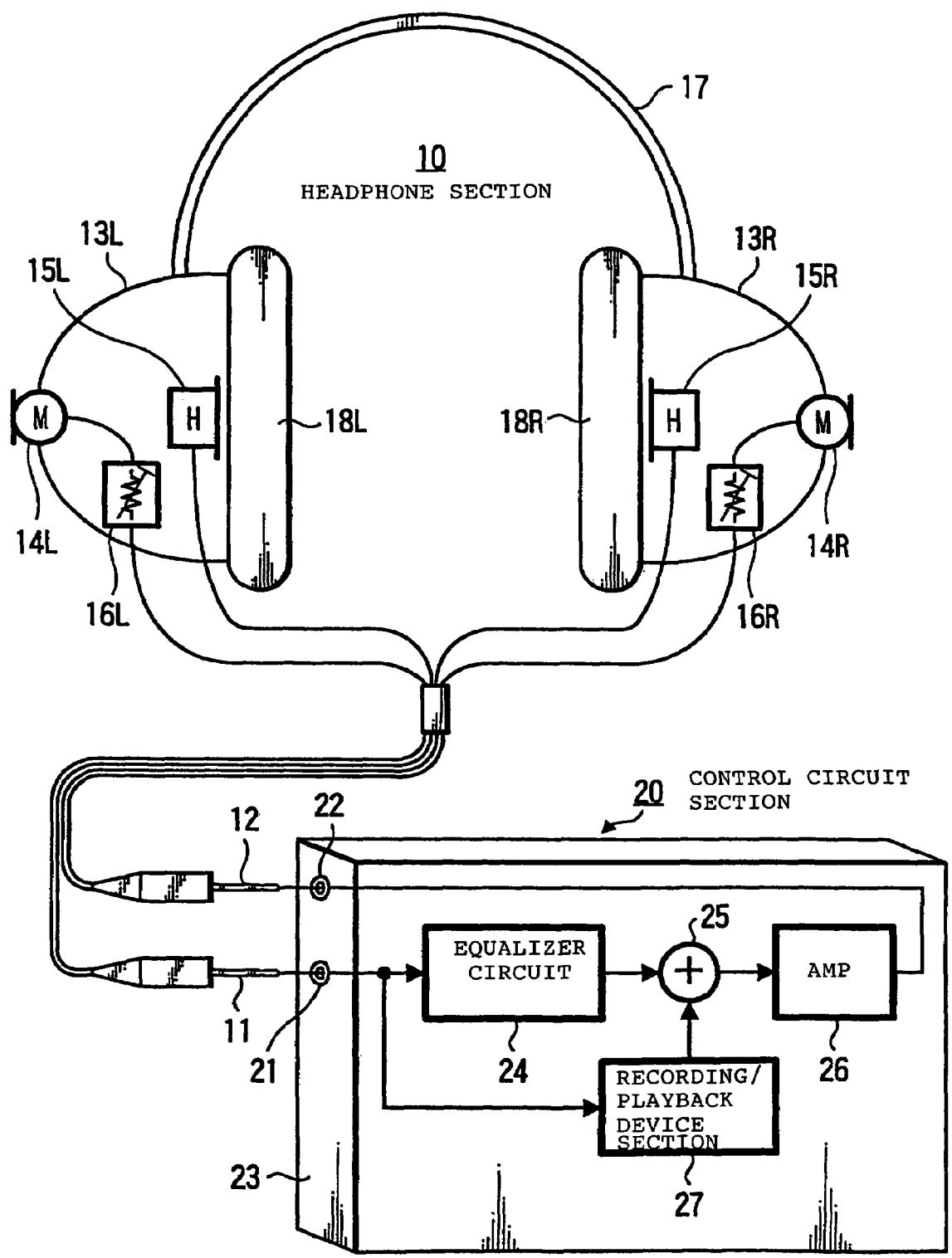
FIG. 1 is a diagram showing the overall configuration example of one embodiment of an acoustic apparatus according to the present invention.

As shown in FIG. 1, an acoustic apparatus of the present embodiment comprises a headphone section 10 and a control circuit section 20. As illustrated, the headphone section 10 and the control circuit section 20 are separately provided, and the headphone section 10 is equipped with a stereo plug 11 as a right and left audio signal output terminal (first output terminal) and a stereo plug 12 as a right and left audio signal input terminal (first input terminal), and the control circuit section 20 is equipped with a jack 21 as a right and left audio signal input terminal (second input terminal) and a jack 22 as a right and left audio signal output terminal (second output terminal) on the side section of the box 23. Inserting the plugs 11, 12 of the headphone section 10 into the jacks 21, 22 of the control circuit section 20 connects the headphone section 10 to the control circuit section 20, and achieves a configuration of the noise canceling headphone later described.

Inside each of the headphone boxes 13L, 13R for right and left ears of the headphone section 10, microphone elements 14L, 14R, driver units 15L, 15R, and gain adjusting sections 16L, 16R are equipped. And the output terminal of microphone elements 14L, 14R are connected to the stereo plug 11 as right and left audio signal output terminals via gain adjusting sections 16L, 16R. The stereo plug 12 as the right and left audio signal input terminal is connected to the driver units 15L, 15R, respectively.

By the way, the headphone boxes 13L, 13R for right and left ears are connected by a belt 17 composed with the elastic material. As for the parts in contact with the user's ears of the headphone box, ear pads 18L, 18R with cushioning material are equipped. And by the belt 17, the headphone section 10 is able to be mounted to the user head. This is hardly different from general headphones.

The control circuit 20 comprises an equalizer circuit 24, adder circuit 25, and AMP 26, and in the present embodiment, when it is connected to the headphone section 10, a feed-forward system noise-canceling circuit is configured.

To the control circuit section 20, a recording/playback device section 27 is equipped, and the audio signal inputted from the jack 21 is supplied to this recording/playback device section 27 as a recording signal and at the same time, a playback audio signal from this recording/playback device section 27 is supplied to the adder circuit 25. This recording/playback device section 27 may be configured in various ways, such as those with, for example, an optical disk or photo-electro-magnetic disk used for a recording medium, or with a magnetic tape.

That is, in the present embodiment, the control circuit section 20 is configured in such a manner as to have the equalizer element and the AMP element for the noise canceling headphone device incorporated in a portable type recording/playback device with, for example, the magnetic tape or photo-electro-magnetic disc used for the recording medium.

And as described above, the equalizer circuit 24 has the phase and amplitude characteristics, that is, frequency characteristics, optimally designed in order to obtain the audio signal for canceling the sound around the user of the headphone section 10 in the control circuit section 20. In addition, the AMP 26 is optimally designed so that the gain of the audio signal for canceling the sound around the user becomes optimum. The AMP 26 has a configuration that enables gain adjustment by semi-fixed resistors, etc.

Furthermore, as described above, in order to absorb the variations of component elements when the noise canceling headphone is divided into the headphone section 10 and the control circuit section 20, the following points are taken into account in the present embodiment.

1) In the case of the present embodiment, as described above, the frequency characteristics of the control circuit section 20 is optimized in order to effectively cancel the surrounding sound, and parts with +5% or +2% tolerances are used for the control circuit section 20 so that the variations of characteristics of the control circuit section 20 become minimum.

Figure 2:
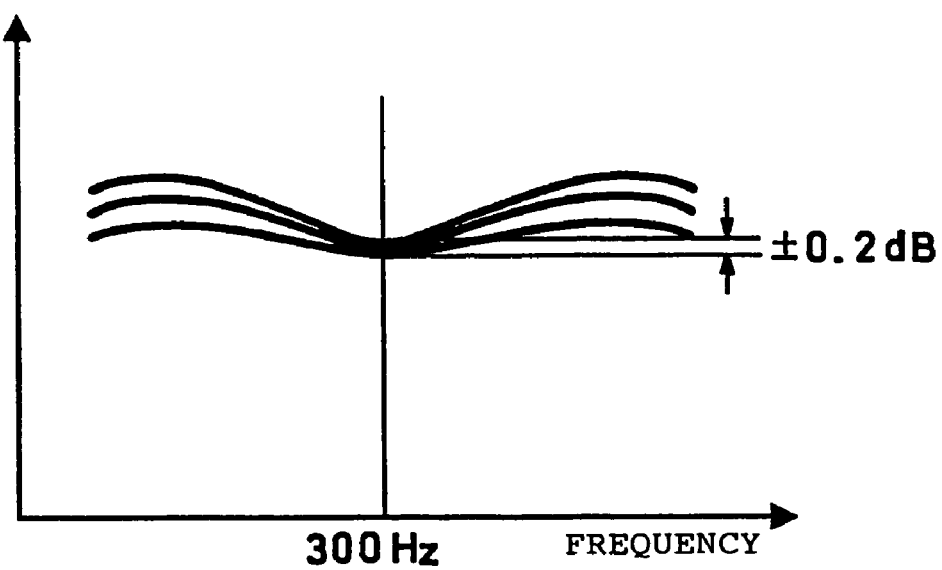
FIG. 2 is a diagram describing an essential portion of one embodiment of an acoustic apparatus according to the present invention.

2) As shown in FIG. 2, the overall gain errors of the equalizer circuit 24 to AMP 26 of the control circuit section 20 are adjusted to be within ±0.2 dB at the position of 300 Hz of the frequency in this example. This adjusted frequency is an example, and a predetermined frequency is chosen between 50 Hz and 1.5 kHz, and preferably between 100 Hz and 1 kHz. This is a band in which noise cancellation is effectively carried out.

3) To jacks 21, 22 of the control circuit section 20 after adjustments, plugs 11, 12 of the headphone section 10 are inserted and connected to connect the headphone section 10 to the control circuit section 20, and, for example, semi-fixed resistors of adjusting sections 16L, 16R of the headphone section 10 are adjusted to vary gains and are set to a condition in which the volume to be canceled is maximized.

As described above, in the present embodiment, in the control circuit section 20, the absolute error of component parts is controlled to be as small as possible, and the error at the headphone section 10 is adjusted one by one by the adjustment elements incorporated into this headphone section, and even when the noise canceling headphone is separated into the headphone section 10 and the control circuit section 20, an acoustic apparatus that is nearly free from variations and that can provide satisfactory canceling effects of surrounding sound is able to be comprehensively achieved.

That is, under the condition in which the headphone section 10 is connected to the control circuit section 20, the audio signal corresponding to the surrounding sound collected by microphone elements 14L, 14R is inputted into the equalizer circuit 24 of the control circuit section 20 through the adjusting sections 16L, 16R, and is controlled in such a manner that the phase and amplitude characteristics become optimum as the audio signal for canceling the surrounding sound. And the output signal of this equalizer circuit 24 is supplied to the AMP 26 through the adder circuit 25, and is made into the optimum gain as an audio signal for canceling the surrounding sound.

The audio signal from the AMP 26 for canceling the sound around the above-described user is supplied to driver units 15L, 15R of the headphone section 10. That is, the driver units 15L, 15R function as sound sources for canceling the sound around the user.

In this way, the sound of a negative phase to that of the surroundings is emitted near the ear (eardrum) of the user, and this is acoustically synthesized with surrounding sound. As a result, the surrounding sound is canceled, and the user is able to hear the sound with surrounding sound reduced.

In this case, music signals, etc. are supplied from the recording/playback device section 27, added at the adder circuit 25, and supplied to the driver units 15L, 15R through the AMP 26, and music is played back. The playback sound the user hear in this case is a clear playback sound with surrounding noise alleviated.

In the present embodiment, so-called binaural recording with superb presence becomes possible with the recording/playback device section 27. That is, microphone elements 14L, 14R are mounted to headphone boxes 13L, 13R, and are able to collect sounds extremely close to those the user hears by its ears. Consequently, recording and playing back the sound collected with the microphone elements 14L, 14R by the recording/playback device section 27 enables the playback of the sound extremely close to the sound the user hears by its ears, and the playback sound with superb presence is able to be obtained.

The reason why this kind of binaural recording is made possible is that the headphone section 10 and the control circuit section 20 are made independent, and the stereo plug 11 is equipped as an output terminal of the audio signal of the sound collected by the microphone elements 14L, 14R.

In the present embodiment, it becomes possible to simultaneously monitor the audio signal from the microphone elements 14L, 14R at the driver units 15L, 15R while it is being recorded at the recording/playback device section 27.

Next description will be made of specific configuration examples of varying gains at adjusting sections 16L, 16R.

Figure 3:
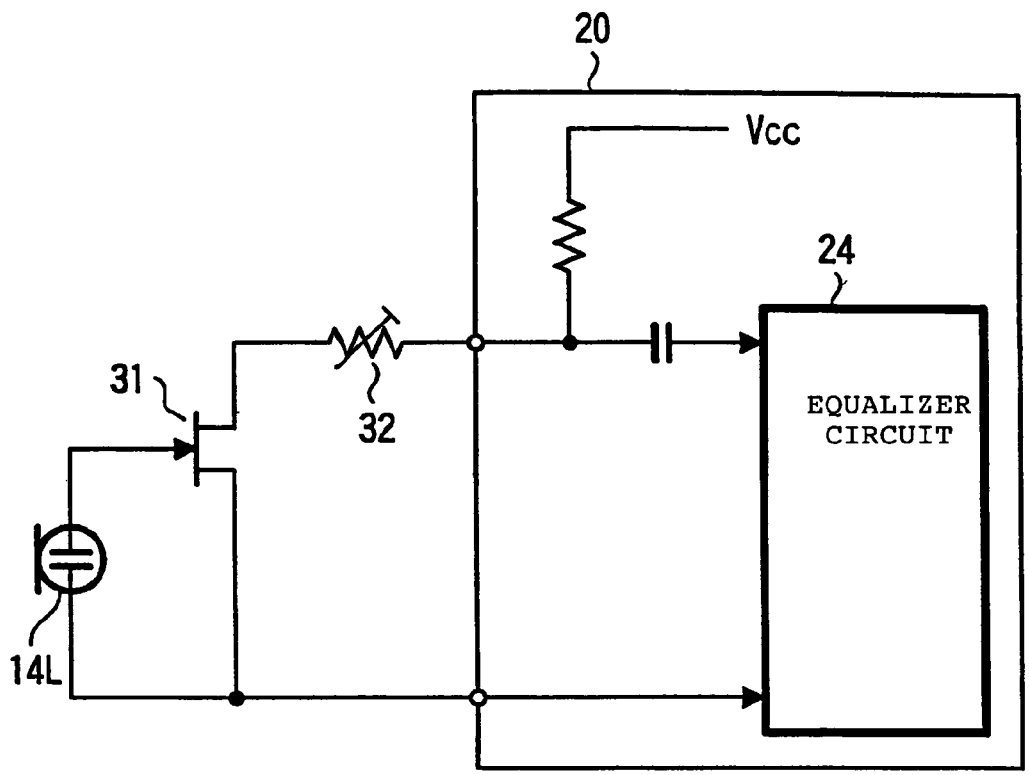
FIG. 3 is a diagram showing a concrete circuit example of part of the embodiment of FIG. 1.

The example of FIG. 3 is the case of the adjusting section 16L, in which the audio signal obtained by acoustic-electric signal conversion at the microphone element 14L is amplified at the FET AMP 31 and taken out, and a semi-fixed resistor 32 is installed in series to this audio signal. By adjusting the resistance value of the semi-fixed resistor 32, gains are adjusted.

Figure 4:
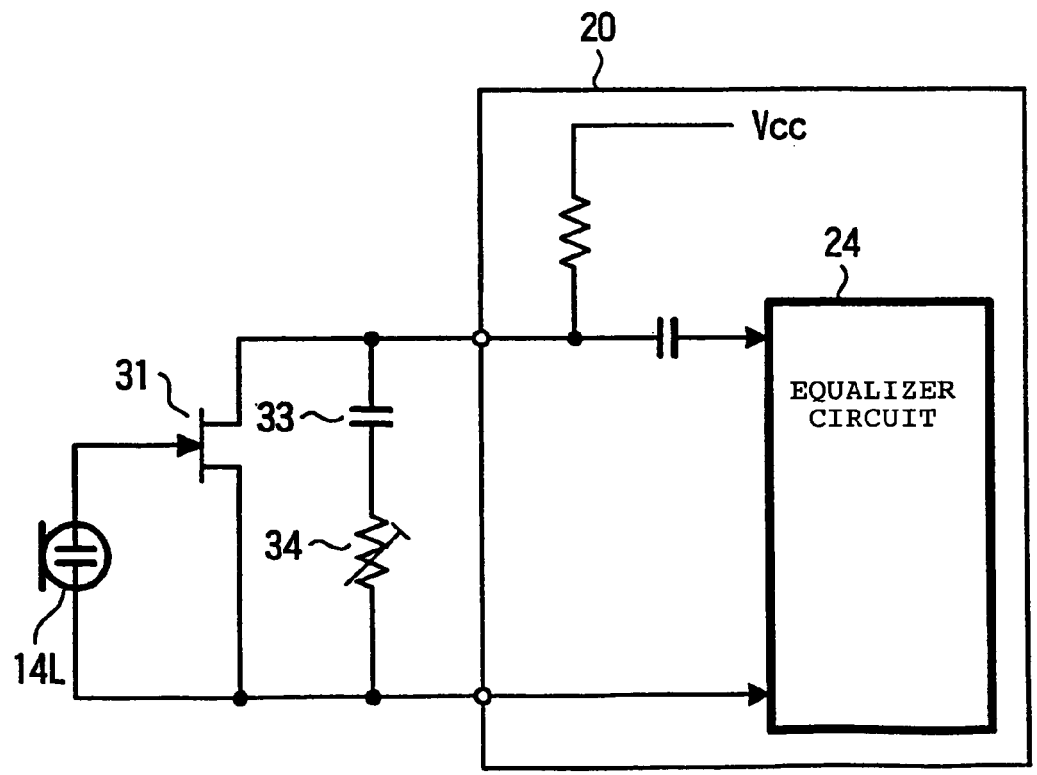
FIG. 4 is a diagram showing a concrete circuit example of part of the embodiment of FIG. 1.

The example of FIG. 4 is similarly the case of the adjusting section 16L, in which a capacitor 33 and a semi-fixed resistor 34 are connected between drain and source of the FET AMP 31. In the case of this example, too, by adjusting the resistance of the semi-fixed resistor 34, gains are adjusted.

Figure 5:
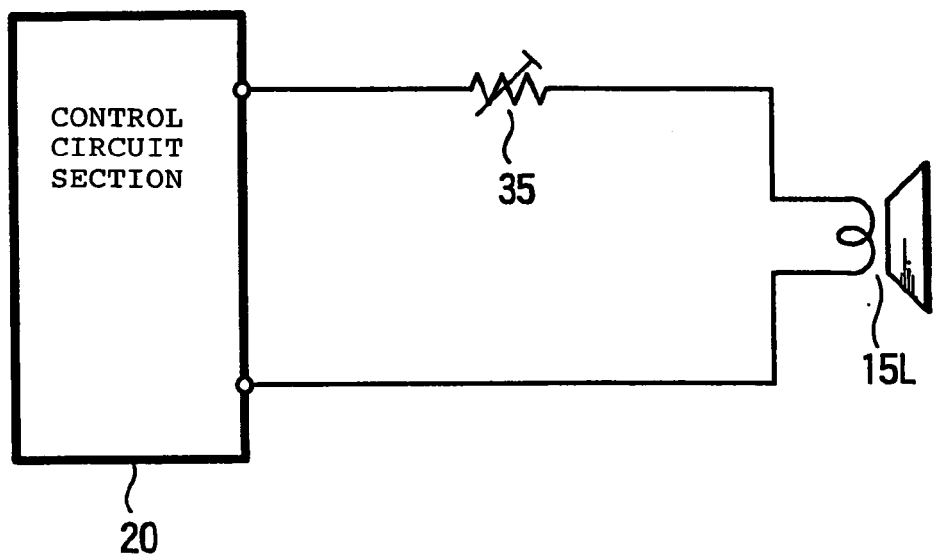
FIG. 5 is a diagram showing a concrete circuit example of part of the embodiment of FIG. 1.
Figure 6:
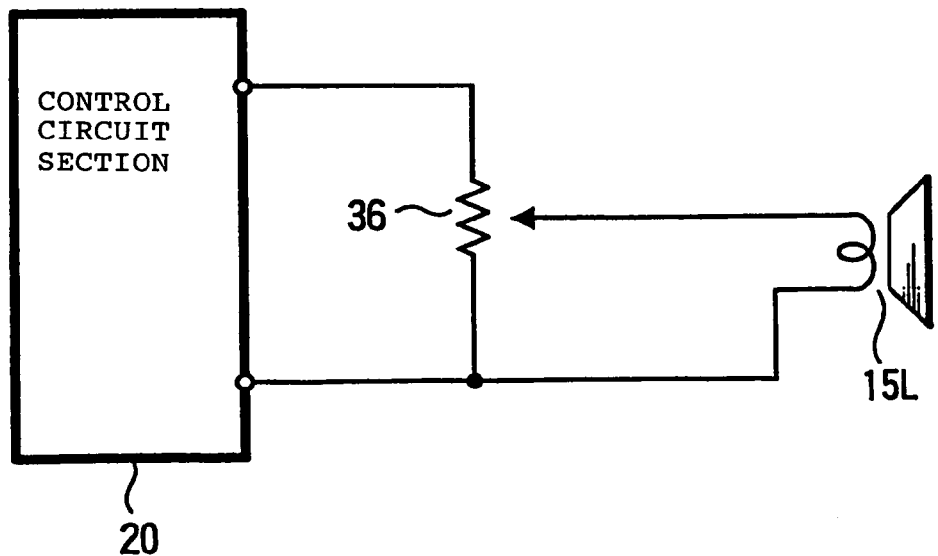
FIG. 6 is a diagram showing a concrete circuit example of part of the embodiment of FIG. 1.

The gain adjusting section is able to be installed on the driver unit 15L, 15R side. FIG. 5 and FIG. 6 show configuration examples in such a case, and examples of driver unit 15L side.

That is, FIG. 5 shows a series type and FIG. 6 a parallel type. That is, in the example of FIG. 5, a semi-fixed resistor 35 is connected in series to the driving coil of the diaphragm of the driver unit 15L. In the example of FIG. 6, the resistance connected in parallel to the driving coil of the diaphragm of the driver unit 15L is configured in such a manner as to be adjusted by the semi-fixed resistor 36.

Examples of the adjusting section of FIG. 3 through FIG. 6 are all configured to adjust gains for every headphone section 10 by the use of the semi-fixed resistor at the time of manufacture, but it is allowed to configure to enable the user to carry out further adjustment at the time of use.

Figure 7:
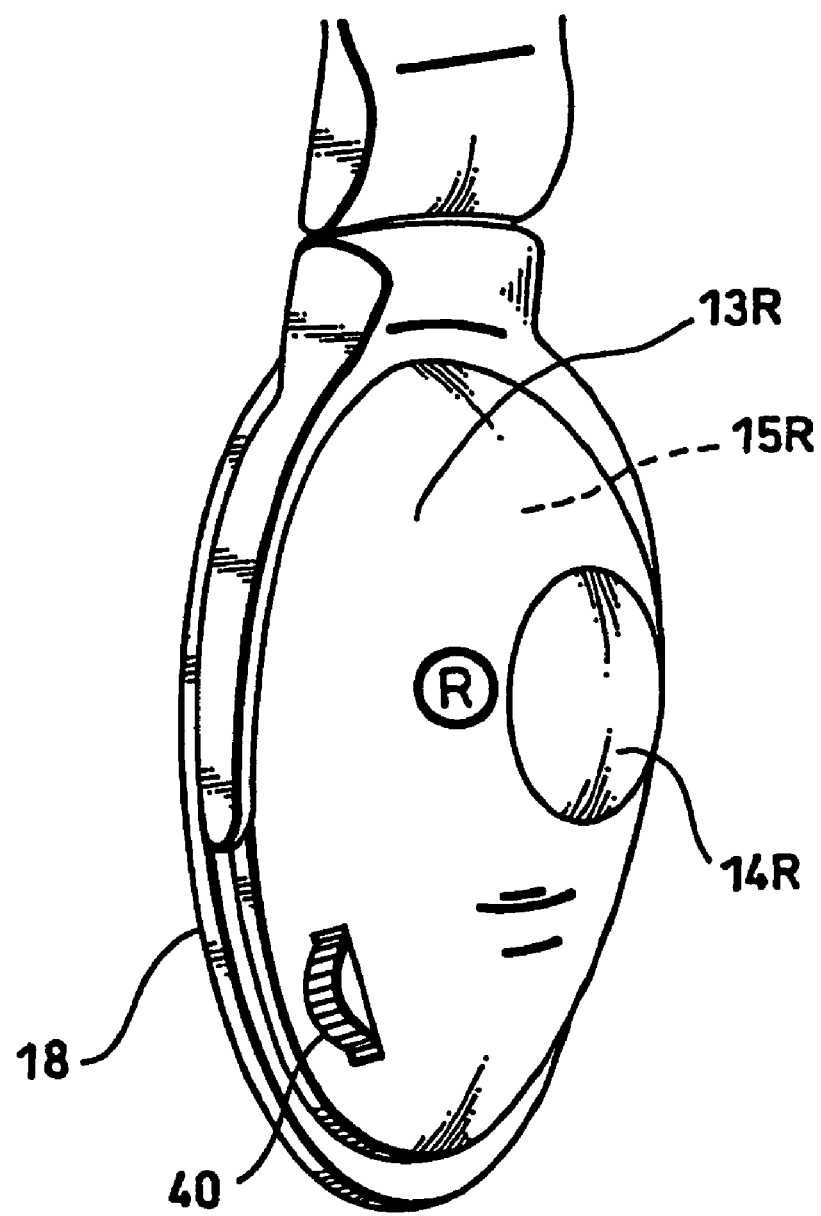
FIG. 7 is a diagram describing an essential portion of another embodiment of the acoustic apparatus according to the present invention.

FIG. 7 shows a configuration example of the headphone box 13L part on the right ear side of the headphone section in that case. As illustrated, in the case of this example, to the headphone box 13L, an adjusting knob 40 of the adjusting section which the user can operate and adjust is installed.

And in the case of this example, semi-fixed resistors 32, 34, 35, 36 of FIG. 3 through FIG. 6 are recommended to have a configuration to divide the semi-fixed resistor part and a variable resistor part which can be adjusted with the adjusting knob 40. That is, the degree that can achieve the predetermined surrounding noise canceling effects is secured by adjusting the semi-fixed resistor part. And by the adjustment by the user using the adjusting knob 40, the canceling effects are further improved. In the case of this example, the adjustable range by the user is narrow, but even if this is not adjusted, the predetermined noise canceling effects are able to be achieved by the adjustment by the semi-fixed resistor.

In other words, adjusting the semi-fixed resistor can achieve adjustment to the degree in which a certain satisfactory level of canceling effects are obtained, but variations of canceling performance associated with inherent attributes such as the profile of user auricle is unable to be compensated for. However, according to this example, the variation portion which is unable to be compensated for is able to be collected by the user operating and adjusting the adjusting knob 40.

As described above, since in the above-mentioned embodiment, the headphone section 10 and the control circuit section 20 are able to be separated, following various advantages are able to be achieved.

The reliability of the headphone section 10 is improved. In other words, the failure rate is expected to lower. Even when one-to-plurality combination is carried out, in which one piece of control circuit section 20 is combined with plural numbers of headphone sections 10, satisfactory cancellation effects as required are able to be obtained.

The cost of the headphone section 10 is able to be minimized, and the replacement cost is able to be reduced at the time of replacing the headphone section due to breakage, etc.

A signal output of the microphone element is able to be utilized and binaural recording is easily achieved. In addition, simultaneous monitoring while the signal output of the microphone element is being recorded is possible.

By enabling the user to adjust and operate the whole or a part of the adjusting section of the headphone section with an adjusting knob, the volume to be canceled is able to be varied, and the user is able to adjust to the optimum cancel point.

The above-mentioned examples are cases in which the control circuit section 20 is a recording/playback device, but needless to say, the control circuit section 20 may have a configuration wherein a device is equipped with an equalizer element for the noise canceling headphone and AMP element without possess the recording/playback functions. The device not equipped with the recording/playback functions is useful as a device used, for example, in a cabin of an aircraft. In the case of device configuration for the aircraft cabin, to the adder circuit 25 of the control circuit section 20, audio sources such as music programs prepared in advance are supplied.

Figure 8:
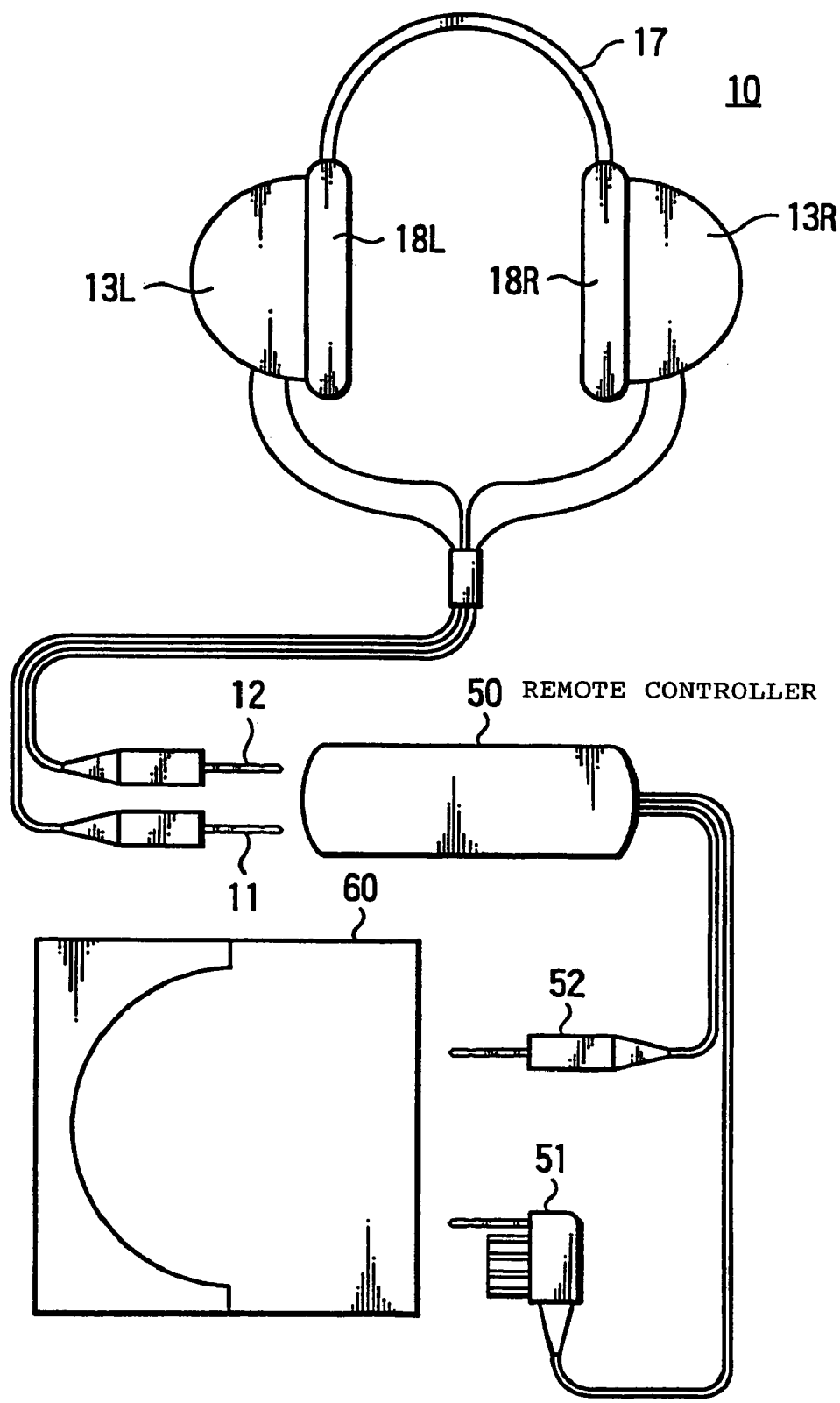
FIG. 8 is a diagram showing the overall configuration example of further another embodiment of the acoustic apparatus according to the present invention.
Figure 9:
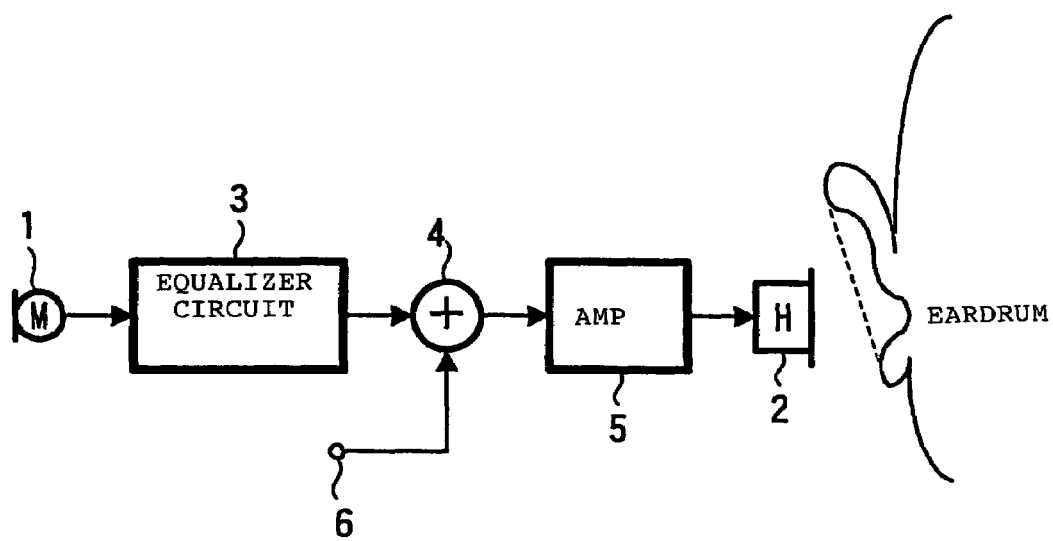
FIG. 9 is a diagram for describing a noise canceling headphone of a feed-forward system.
Figure 10:
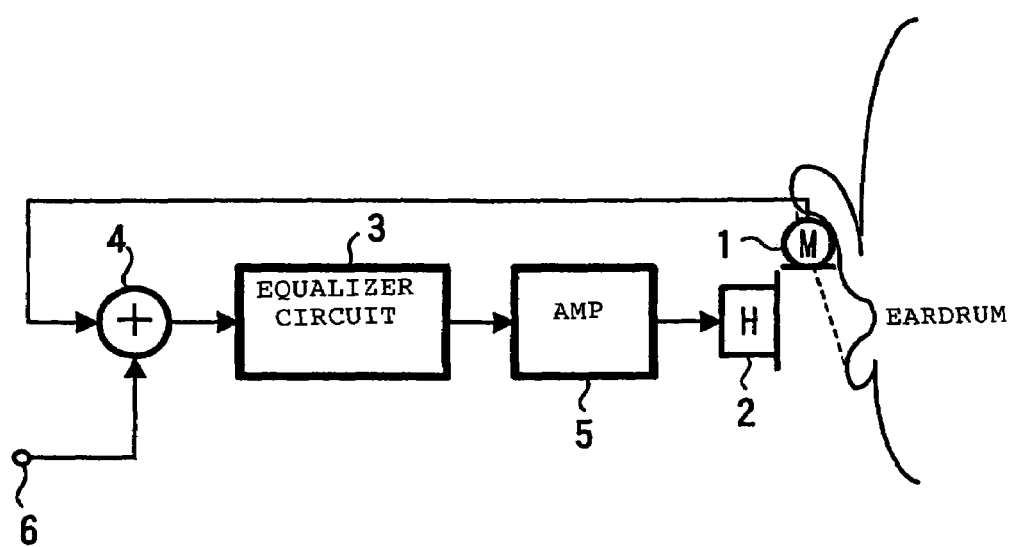
FIG. 10 is a diagram for describing a noise canceling headphone of a feedback system.

The control circuit section 20 may have a configuration of a remote controller of a portable type recording/playback device. FIG. 8 shows the external configuration diagram in that case.

That is, in the example of FIG. 8, plugs 11 and 12 of the headphone section 10 are connected to jacks installed in the remote controller 50, respectively. Inside the remote controller 50, the equalizer circuit 24, adder circuit 25, and circuit part of AMP 26 of the control circuit section 20 in FIG. 1 are mounted, and in the case of this example, a configuration of a noise canceling headphone device is realized by the headphone section 10 and the remote controller 50.

And this remote controller 50 is equipped with a plug 51 plurally connected to the remote control terminal and headphone terminal of the recording/playback device 60 in order to provide functions for remotely controlling the recording/playback device 60 as well as functions to receive playback signals from the recording/playback device 60 and supply them to the adder circuit 25.

In addition, the remote controller 50 of this example is equipped with a plug 52 for being inserted into a jack as an audio signal input terminal of the recording/playback device 60, and has a function to supply audio signals from microphone elements 14L, 14R of the headphone section 10 to the audio signal input terminal of the recording/playback device 60. With these functions, in the recording/playback device 60, binaural recording becomes possible, and simultaneous monitoring in that case is also possible.

In the above-mentioned embodiments, description is made of the feed-forward system for the noise canceling system, but in the present invention, it is needless to say that the same configuration is able to be achieved whether the feedback system is used for the noise canceling system or digital system noise canceling system is used.

POSSIBILITY FOR INDUSTRIAL USE

This device is applied to the so-called noise canceling headphone for collecting noise around the user by the microphone with a headphone built into a box, analyzing the noise, outputting the sound of a negative phase to the noise, and reducing the surrounding noise. In this case, the noise canceling headphone is utilized in the aircraft for listening to music with engine noise reduced.

The invention claimed is:

1. An acoustic apparatus comprising:
a headphone section mounted on a user's head having first and second headphone boxes arranged respectively on the ears of the user and having first and second microphone elements mounted respectively on the first and second headphone boxes for detecting sound around the user and signal acoustic transducing elements mounted respectively in the first and second headphone boxes functioning as sound sources with first output terminals for outputting microphone audio signals collected by the first and second microphone elements and first input terminals for inputting audio signals supplied to the first and second signal acoustic transducing elements; and
a control circuit section separate and independent from the headphone section and having second input terminals connected to the first output terminals and second output terminals connected to the first input terminals for controlling at least frequency characteristics and gain characteristics of the microphone audio signals from the first and second microphone elements of the headphone section input through the second input terminals, for generating a cancel audio signal for canceling effects of the sound around the user in the signals fed to the first and second signal acoustic transducing elements, and for supplying the cancel audio signal to the first and second signal acoustic transducing elements of the headphone section through the second output terminals, whereby ambient sound around the user is cancelled in a range of 50 Hz to 1.5 kHz, said control circuit section further including recording means for recording the microphone audio signals output from the first and second microphone elements as binaural audio signals.

2. The acoustic apparatus according to claim 1, wherein the control circuit section further comprises:
means for adding different audio signals to the cancel audio signal using a signal audio converter element.

3. The acoustic apparatus according to claim 1, wherein the control circuit section further comprises:
means for adding different audio signals to the cancel audio signal using a signal audio converter element as a sound source; and
a remote control configured to supply remote-control signals for remotely controlling output of the different audio signals.

4. An acoustic apparatus comprising:
a headphone section mounted on a user's head, having first and second headphone boxes arranged respectively on the ears of the user, first and second microphone elements mounted on the first and second headphone boxes for detecting sound around the user first and second signal acoustic transducing elements arranged in the first and second headphone boxes functioning as sound sources, first output terminals, an adjusting section for adjusting outputs of microphone audio signals collected by the first and second microphone elements, and first input terminals for inputting a cancel audio signal supplied to the first and second signal acoustic transducing elements, and a control circuit section arranged in a housing separate and independent from the headphone section and having a second input terminals connected to the first output terminals and second output terminals connected to the first input terminals for controlling at least frequency characteristics and gain characteristics of the microphone audio signals from the first and second microphone elements of the headphone section input through the second input terminals, for generating the cancel audio signal that can serve as a sound source for canceling effects of the sound around the user, and for supplying the cancel audio signal to the first and second signal acoustic transducing elements of the headphone section through the second output terminals, whereby ambient sound around the user is cancelled in a range of 5 Hz to 1.5 kHz, said housing also having arranged therein recording means for recording the microphone audio signals from the first and second microphone elements as binaural signals.

5. The acoustic apparatus according to claim 4, wherein an amplifier section is included in each first and second headphone box behind the adjusting section for amplifying the microphone audio signals from the first and second microphone elements and for adjusting the microphone audio signals from the first and second microphone elements, where gains are controlled by amplifying the microphone audio signals.

6. The acoustic apparatus according to claim 4, wherein an amplifier section for generating signals serving as a sound source for canceling the sound around the user and adjusting means for adjusting an output level of the amplifier section are provided in each first and second headphone box, and gains of the cancel audio first and second signal input to the signal acoustic transducing elements are controlled.

7. The acoustic apparatus according to claim 4, wherein an adjusting section adjusts the microphone audio signals from the first and second microphone elements that serve as sound sources for canceling the effects of the sound around the user and adjusts the microphone audio signals from the first and second microphone elements in the first and second headphone boxes, said adjusting means having operating means operable by the user from outside the first and second headphone boxes, and an amplifier section for amplifying the microphone audio signals adjusted at the adjusting section.

8. An acoustic apparatus comprising:

a recording/playback device;

a headphone section mounted on a user's head, having first and second headphone boxes arranged respectively on the ears of the user and having first and second microphone elements for detecting sound around the user and first and second signal acoustic transducing elements functioning as sound sources with first output terminals for outputting microphone audio signals collected by the first and second microphone elements and first input terminals for inputting a cancel audio signal supplied to the first and second signal acoustic transducing elements; and a remote control connected to said recording/playback device for controlling operation of said recording/playback device and feeding the microphone audio signals to the recording/playback device for recording as binaural signals, said remote controller being separate and independent from the headphone section and including a control section having second input terminals connected to the first output terminals and second output terminals connected to the first input terminals for controlling at least frequency characteristics and gain characteristics of the microphone audio signals from the first and second microphone elements of the headphone section input through the second input terminals, with said frequency characteristics and gain characteristics being adjusted to achieve a predetermined level at a predetermined frequency between 50 Hz and 1.5 kHz, for generating the cancel audio signal that can cancel the ambient sound around the user within a range of 50 Hz to 1.5 kHz, and for supplying the cancel audio signal to the first and second signal acoustic transducing elements of the headphone section through the second output terminals.

9. An acoustic apparatus comprising:

a headphone section mounted on a user head, having a microphone elements mounted on the first and second headphone boxes for detecting sound around the user and first and second signal acoustic transducing element functioning as sound sources with first output terminals for outputting microphone audio signals collected by the first and second microphone elements and first input terminals for inputting a cancel audio signal supplied to the first and second signal acoustic transducing elements;

a control circuit section arranged in a housing separate and independent from the headphone section and having second input terminals connected to the first output terminals and a second output terminals connected to the first input terminal for controlling at least frequency characteristics and gain characteristics of the microphone audio signals from the first and second microphone elements of the headphone section input through the second input terminals, for generating the cancel audio signal for canceling the effects of the ambient sound around the user within a range of 50 Hz to 1.5 kHz, and for supplying the cancel audio signal to the first and second signal acoustic transducing elements of the headphone section through the second output terminals, and a recording/playback device arranged in the housing for recording the microphone audio signals from the first and second microphone elements as binaural audio signals; and a circuit configuration for canceling the surrounding sound used by the control circuit section that is of a feed-forward system.

10. An acoustic apparatus comprising:

a recording/playback device;

a headphone section mounted on a user's head, having first and second headphone boxes arranged on respective ears of the user and having first and second microphone elements arranged respectively on the first and second headphone boxes for detecting sound around the user and first and second signal acoustic transducing elements functioning as sound sources housed in first and second headphone boxes, respectively, with first output terminals for outputting microphone audio signals collected by the first and second microphone elements and first input terminals for inputting a cancel audio signal supplied to the first and second signal acoustic transducing elements for canceling effects of ambient sound around the user within a range of 50 Hz to 1.5 kHz;

a remote controller connected to said recording/playback device for controlling operation of said recording/playback device and feeding the microphone audio signals to the recording/playback device for recording as binaural audio signals, said remote controller being separate and independent from the headphone section and including a control circuit section having second input terminals connected to the first output terminals and second output terminals connected to the first input terminals for controlling at least frequency characteristics and gain characteristics of the microphone audio signals from the first and second microphone elements of the headphone section input through the second input terminals, for generating the cancel audio signal for canceling effects of the sound around the user, and for supplying the cancel audio signal to the first and second signal acoustic transducing elements of the headphone section through the second output terminals; and a circuit configuration for canceling the effects of the sound surrounding the user used by the control circuit section that is of a feedback system.

* * * * *